United States Patent [19]

Piraino et al.

[11] Patent Number: 5,021,448

[45] Date of Patent: Jun. 4, 1991

[54] METHOD OF REDUCING SERUM URIC ACID AND/OR INCREASING RENAL URIC ACID CLEARANCE WITH THROMBOXANE SYNTHETASE INHIBITOR INHIBITOR AND/OR THROMBOXANE RECEPTOR ANTAGONIST

[75] Inventors: Anthony J. Piraino, Media; Steven D. Saris, Ardmore, both of Pa.

[73] Assignee: Ciba-Geigy Corporation, Ardsley, N.Y.

[21] Appl. No.: 483,160

[22] Filed: Feb. 22, 1990

[51] Int. Cl.$^5$ .................. A61K 31/415; A61K 31/40; A61K 31/34; A61K 31/335; A61K 31/265; A61K 31/18; A61K 31/135; A61K 31/095; A61K 31/10; A61K 31/075; A61K 31/045; A61K 31/05; A61K 31/44

[52] U.S. Cl. .................. 514/415; 514/385; 514/390; 514/408; 514/410; 514/412; 514/422; 514/427; 514/429; 514/461; 514/449; 514/468; 514/469; 514/512; 514/601; 514/602; 514/604; 514/646; 514/650; 514/706; 514/709; 514/715; 514/717; 514/719; 514/720; 514/724; 514/729; 514/730; 514/736; 514/891; 514/332

[58] Field of Search ............... 514/385, 390, 408, 410, 514/415, 427, 449, 601, 602, 604, 646, 650, 709, 715, 717, 730, 736, 332

*Primary Examiner*—Stanley J. Friedman
*Assistant Examiner*—Terry Wilson
*Attorney, Agent, or Firm*—Irving M. Fishman; JoAnn Villamizar

[57] ABSTRACT

A method of reducing serum uric acid and/or increasing renal clearance of uric acid in a mammal in need thereof comprising administering to such mammal a uricosuric effective amount of a thromboxane synthetase inhibitor, a thromboxane receptor antagonist, or both in a combined uricosuric effective amount is disclosed. Compositions having one or more of the foregoing in combination with one or more known uricosurics are also set forth.

10 Claims, No Drawings

METHOD OF REDUCING SERUM URIC ACID AND/OR INCREASING RENAL URIC ACID CLEARANCE WITH THROMBOXANE SYNTHETASE INHIBITOR INHIBITOR AND/OR THROMBOXANE RECEPTOR ANTAGONIST

FIELD OF THE INVENTION

The present invention relates to the field of thromboxane synthetase inhibitors, thromboxane receptor antagonists, and uric acid and disease states due to an excess thereof such as gout, gouty arthritis, etc.

BACKGROUND OF THE INVENTION

Uric acid is a naturally occurring metabolite of a number of typically ingested compounds, especially xanthines such theobroma (in chocolate), caffeine, etc, and is generally disposed of by the body by execretion into the urine from the blood. When uric acid production is high or its elimination from the body is low so that serum levels are at high levels for considerable periods of time, there is the risk that uric acid crystals will begin to form at various points in the body. When these crystals become large enough to become painful, clinical conditions such as gout, gouty arthritis, and uric acid stones (urinary and elsewhere) result. Such situations may result from disease states or may be drug induced, for example, serum uric acid levels are elevated with a substantial number of diuretic drugs, most notably the thiazide diuretics, and upon cytotoxic antineoplastic agent administration and cyclosporin A. Clinical conditions associated with elevated serum uric acid include gout, gouty arthritis, gouty nephropathy, eclampsia, and diseases that involve accelerated formation and destruction of blood cells.

Upon diagnosis of the elevated serum uric acid, therapies which are begun have included dietary intervention (to reduce intake of substances which are metabolized to uric acid), intervention in the metabolic pathways leading to uric acid (i.e. allopurinol which inhibits xanthine oxidase from converting hypoxanthine and xanthine to uric acid) and uricosurics such as probenecid or sulfinpyrazone, which increase the amount of uric acid resulting in the urine by improving its passage into the urine from the blood or by interfering in its reuptake.

Overwhelmingly, in recent times the mainstay of treatment for excess uric acid conditions has been the use of allopurinol. The typical uricosurics have required doses of large amounts [cite probenecid dosage] so as to make compliance difficult. In addition, large volumes of fluids have been necessary for both maintaining the urine concentration of uric acid low enough and to permit the uricosuric to sufficiently pass through the system. In addition standard uricosurics have their own problems associated therewith. For example, sulfinpyrazone should not really be given to patients with a history of peptic ulcer disease, phenylbutazone has this same problem as well as severe blood dyscrasias associated with its use such that it is not used for chronic administration, probenecid should be administered to patients with history of peptic ulcer disease only with caution; anticoagulents such as coumarins and indandiones and oral hypoglycemics of the sulfonylurea group, while having some uricosuric property are unsuited to being used for their uricosuric property generally due to their primary activities.

OBJECTS OF THE INVENTION

It is therefore an object of the invention to provide a new uricosuric which is free of the above defects.

Another object of the invention is to provide a new treatment for excess serum uric acid and conditions resulting therefrom.

Yet another object of the invention is to provide a new combination composition or therapy for treating elevated serum uric acid.

SUMMARY OF THE INVENTION

Surprisingly, it has now been found that the above objects and others can be achieved by administering to a mammal in need thereof a serum uric acid reducing effective amount of a thromboxane synthetase inhibitor, or a thromboxane receptor antagonist or a combined effective serum uric acid lowering amount of combinations of thromboxane synthetase inhibitors and/or thromboxane receptor antagonists. The above combinations and therapies can be alone or combined with other uricosurics and/or uric acid synthesis inhibitors, such as allopurinol.

DETAILED DESCRIPTION OF THE INVENTION

The instant invention is a method of reducing serum uric acid levels in a mammal, especially humans, in need thereof by administering to such mammal an effective serum uric acid reducing amount of (i) a thromboxane synthetase inhibitor or (ii) a thromboxane receptor antagonist or (iii) a thromboxane synthetase inhibitor and thromboxane receptor antagonist combination, alone or with other uricosurics and/or uric acid synthesis inhibitors, such as allopurinol.

Also within the invention are compositions used in the practice of the method, which compositions comprise an effective serum uric acid reducing amount of (i) a thromboxane synthetase inhibitor, (ii) a thromboxane receptor antagonist, or (iii) a combination of a thromboxane synthetase inhibitor and thromboxane receptor antagonist.

Methods of treatment within the instant invention include serum uric acid lowering responsive conditions, such as gout, gouty arthritis, gouty nephritis, eclampsia, secondary chronic hyperuricemia of polycythemia vera, of myeloid metaplasia, or of other blood dyscrasias, and concomitant therapy with diuretic agents or cytotoxic antineoplastic agents to offset the increase in serum uric acid levels associated therewith.

Thromboxane synthetase inhibitors useful in the instant invention include 2-pyridyl-indoles and 2-imidazolyl-indoles such as those in U.S. Pat. Nos. 4,478,842 and 4,511,573; imidazo[1,5-a] puridines of U.S. Pat. No. 4,444,775; dazmegrel; pirmagrel; dazoxiben; furegrelate; (E)-4-(1-imidazolyl methyl) cinnamic acid hydrochloride; (E)-7-phenyl-(3-pyridyl)-6-heptanoic acid; 1-(3-benzyl-oxy-1(E)octenyl)imidazole; 5-(1H-imidazol-1-yl)-2-methyl-4-(2,4,6-trimethylphenyl)benzyl alcohol; sodium 4-[-hydroxy-5-(1-imidazolyl)-2-methylbenzyl]-3,5-dimethylbenzoate dihydrate; 5,6-dihydro-7-(1H-imidazolyl)-2-naphthalene carboxylic acid; methyl-5-[2-(1-imidazolyl)-ethoxy]-thiopene-2-carboxylic acid; 4-[1-[(1-imidazolyl)methyl]-2[(4-methoxy phenyl)-methoxy]-ethoxy]-dimethyl pentanoic acid; and 2-methyl-3-[4-(3-pyridinyl methyl)phenyl]-2-propenoic acid sodium; RO-24-0238 (Amer. Rev. Resp. Dis. 139 (4, part 2) A611, 1989); R-68070 (arch. int Pharmacodyn. 298, 293–304, 1989); DP-1904 (J. Mol. Cell. Cardiol. 21 (Suppl. 2) S 118 abstract 352, 189); RS-5186 (J. Md. Cell. Cardiol. 21 (Suppl. 2) S 98, abstract 293, 1989) and the free acid thereof (J. Med. Chem. 32(b) 1265–1272, 189); among others. The only limitation to the utility of thromboxane synthetase inhibitors in the present invention is that they be pharmaceutically acceptable. Especially useful in this regard are: 1-(7-carboxy heptyl)-3-methyl-2-(3-pyridyl)indole; 5-(5-carboxypentyl)-imidazo[1,5-a]pyridine; and 1-methyl-2-)3-pyridyl-3(5-carboxypentyl)indole. Other thromboxane synthetase inhibitors which can be used in the invention are disclosed in U.S. Pat. Nos. 4,619,941; 4,511,573; 4,487,842; 4,611,059; 4,520,207; 4,610,981; 4,607,046; 4,602,016; 4,593,029; 4,590,203; 4,588,732; 4,576,957; 4,568,687; 4,562,199; 4,599,336; 4,590,200; 4,584,379; 4,575,512; 4,568,685; 4,542,145; 4,563,446; 4,555,519; 4,555,516; 4,536,505; 4,551,468; 4,518,602; among others.

The uricosuric effective amounts of the thromboxane synthetase inhibitors are the amounts of these substances necessary to effect thromboxane synthetase inhibition. Such amounts are known in the art, as typified by the above U.S. Patents and articles.

Thromboxane receptor antagonists suitable for use in the instant invention include, inter alia: 7-(3-(3-cyclohexyl-3-hydroxy-1-propenyl)-7-oxabicyclo(2.2.1-)hept-2-yl)-5-heptenoic acid; SQ 28913 and its analogs as set forth in J. Med. Chem. 32(5) 974–984, 1989; RS-61756-007 (J. Pharm. Pharmacol. 41(5) 347–349, 1989); ONO-3708 (Euro. J. Pharmacol. 163 (2/3) 253–261, 1989) and [p-(2-benzenesulfonamidoethyl)phenoxy]acetic acid, as well as those disclosed in U.S. Pat. Nos. 4,588,742, 4,239,778, and 4,182,876; to name a few.

The uricosuric effective amounts of the thromboxane receptor antagonists are those amounts necessary to obtain thromboxane receptor antagonism. Such amounts can be found in the above mentioned U.S. Patents and articles.

The thromboxane synthetase inhibitor and/or thromboxane receptor antagonists may be administered alone or in conjunction with other uricosurics or xanthine oxidase inhibitors, when being used to offset the hyperuricemic effects of other drugs or when the foregoing combination therapy is indicated. They may be administered, in appropriate circumstances by the same or different routes administration and as a single or as separate compositions.

Compositions of the thromboxane synthetase inhibitors suitable for use in the practice of the method of this invention include those compositions generally known in the art for use with thromboxane synthetase inhibitors to obtain thromboxane synthetase inhibition. These are exemplified by the compositions set forth (and their suitable components) in the U.S. Patents relating to thromboxane synthetase inhibitors identified earlier.

Similarly, compositions of the thromboxane receptor inhibitors suitable for use in the instant method include those generally known in the art for use with thromboxane receptor antagonists to obtain thromboxane receptor antagonism. These are exemplified by the compositions mentioned in the thromboxane receptor antagonist U.S. Patent discussed above.

Combinations of thromboxane synthetase inhibitor compositions and thromboxane receptor antagonist compositions are also suitable for use in the instant method.

The instant invention also relates to new compositions within the scope of those generally mentioned above. The new compositions comprise a) a hyperuricemic drug, a cytotoxic antineoplastic drug, a diuretic, a xanthine oxidase inhibitor, or a uricosuric other than either a thromboxane synthetase inhibitor or thromboxane receptor antagonist and b) at least one of a thromboxane synthetase inhibitor or a thromboxane receptor antagonist.

The new compositions are more limited in their pharmaceutically acceptable adjuvants than the compositions generally suitable for the method of treatment or prevention set out above in that those components must also be compatible with the non-thromboxane synthetase inhibitor non-thromboxane receptor antagonist component.

The compositions useful in the present invention can be of any suitable dosage form, such as tablets, capsules, powders, solution, suspensions, immediate and sustained release. Procedures for making such dosage forms are well within the abilities of one of ordinary skill in the art.

These new compositions contain a sufficient amount of the thromboxane synthetase inhibitor and/or thromboxane receptor antagonist such that at the point in time of administration to a mammal, the dose delivered is sufficient to obtain thromboxane synthetase inhibition and/or thromboxane receptor antagonism and thereby reduce or prevent the hyperuricemic states. Typically, this dose for thromboxane synthetase inhibitors is in the range of about 0.01 to about 100 mg/kg/day; preferably about 0.05 to about 50 mg/kg/day; more preferably about 0.1 to about 25 mg/kg/day. The same general dosage range applies to the thromboxane receptor antagonists. Alternative dosage ranges can be found in the aforementioned U.S. Patents and literature references mentioned above.

The following examples are presented to exemplify the invention without limiting its scope.

EXAMPLE I

| Solution for Oral Use | |
| --- | --- |
| Ethanol USP | 12.5% by volume |
| 1-(7-carboxyheptyl)-3-methyl-2-(3-pyridyl)indole | 10 g |
| [p-(2-benzensulfonamido-ethyl)phenoxy]acetic acid | 10 g |
| Vehicle q.s. | 1 liter |

The vehicle is a mixture of olive oil and poloxyethylated oleic glycerides. The solution is diluted in milk or juice just prior to ingestion.

EXAMPLE II

| Intravenous Solution | |
| --- | --- |
| 5-(5-carboxypentyl)imidazolyl5-a]pyridine hydrochloride | 20 g |
| Oxyethylated castor oil | 650 g |
| Ethanol USP | 32.9% by volume to 1 liter |

The appropriate dose is diluted just prior to administration with 20 to 100 times as much normal saline or 5% dextrose and administered over a number of hours.

What we claim:

1. A method of treating or preventing hyperuricemia in a mammal in need thereof comprising administering to said mammal a hyperuricemia reducing or preventing effective amount of
- a) a thromboxane synthetase inhibitor;
- b) a thromboxane receptor antagonist; or both a) and b).

2. The method of claim 1 wherein said thromboxane synthetase inhibitor is selected from 1-(7-carboxy heptyl)-3-methyl-2-(3-pyridyl)indole; 5-(5-carboxypentyl)-imidazo[1,5-a]pyridine; and 1-methyl-2-(3-pyridyl)-3-(5-carboxypentyl)indole; and the pharmaceutically acceptable salts thereof.

3. The method of claim 2 wherein said pharmaceutically acceptable salt is the hydrochloride salt.

4. The method of claim 1 wherein
- a) a thromboxane synthetase inhibitor; or
- b) both a thromboxane synthetase inhibitor and a thromboxane receptor antagonist is administered.

5. The method of claim 4 wherein both a thromboxane synthetase inhibitor and a thromboxane receptor antagonist are administered.

6. The method of claim 1 wherein said thromboxane receptor antagonist is selected from 7-(3-(3-cyclohexyl-3-hydroxy-1-propenyl)-7-oxabicyclo(2.2.1)hept-2-yl)-5-heptenoic acid and [p-(2-benzenesulfonamidoethyl)-phenoxy]acetic acid.

7. A composition for the prevention or reduction of hyperuricemia comprising
- a) an effective hyperuricemia reducing or preventing amount of
  - (i) a thromboxane synthetase inhibitor;
  - (ii) a thromboxane receptor antagonist; or
  - (iii) both a thromboxane synthetase inhibitor and a thromboxane receptor antagonist; and
- b) an effective amount of at least one of
  - (i) a diuretic;
  - (ii) a cytotoxic antineoplastic;
  - (iii) a uricosuric not within paragraph (a);
  - (iv) a xanthine oxidase inhibitor; or
  - (v) an agent other than b)(i)-b(v) useful in the treatment of at least one condition selected from gout, gouty arthritis, gouty nephritis, eclampsia, polycythemia vera, myeloid metaplasia and other blood dyscrasias; or
  - (vi) cyclosporin A.

8. The composition of claim 7 wherein said thromboxane synthetase inhibitor is selected from 1-(7-carboxy heptyl)-3-methyl-2-(3-pyridyl)indole; 5-(5-carboxypentyl)-imidazo[1,5-a]pyridine; 1-methyl-2-(3-pyridyl)-3-(5-carboxypentyl)indole; and a pharmaceutically acceptable salt thereof.

9. The composition of claim 8 wherein said pharmaceutically acceptable salt is the hydrochloride salt.

10. The method of claim 1 wherein said hyperuricemia is associated with a disease state selected from gout, gouty arthritis, gouty nephritis, pre-eclampsia, eclampsia, polycythemia vera, myeloid metaplasia, and other blood dyscrasias, or with the administration of cyclosporin A.

* * * * *